US008958994B2

(12) United States Patent  (10) Patent No.: US 8,958,994 B2
Padilla et al.  (45) Date of Patent: Feb. 17, 2015

(54) NON-CONTACT ACOUSTIC SIGNAL PROPAGATION PROPERTY EVALUATION OF SYNTHETIC FIBER ROPE

(75) Inventors: Luis S. Padilla, Charlotte, NC (US); Philip Bull, Cheswardine (GB); Roger L. Royer, Jr., Williamsburg, PA (US); Steven E. Owens, Bellefonte, PA (US)

(73) Assignee: Actuant Corporation, Menomonee Falls, WI (US)

( * ) Notice: Subject to any disclaimer, the term of this patent is extended or adjusted under 35 U.S.C. 154(b) by 512 days.

(21) Appl. No.: 13/318,447

(22) PCT Filed: May 5, 2010

(86) PCT No.: PCT/US2010/033767
§ 371 (c)(1),
(2), (4) Date: Nov. 1, 2011

(87) PCT Pub. No.: WO2010/129701
PCT Pub. Date: Nov. 11, 2010

(65) Prior Publication Data
US 2012/0053852 A1  Mar. 1, 2012

Related U.S. Application Data

(60) Provisional application No. 61/215,527, filed on May 5, 2009, provisional application No. 61/215,496, filed on May 6, 2009.

(51) Int. Cl.
*G01N 29/04* (2006.01)
*G06F 19/00* (2011.01)
*G01N 29/07* (2006.01)
*G01N 29/22* (2006.01)

(52) U.S. Cl.
CPC .............. *G01N 29/07* (2013.01); *G01N 29/223* (2013.01); *G01N 2291/02827* (2013.01); *G01N 2291/102* (2013.01); *G01N 2291/2626* (2013.01)
USPC .............. 702/34; 73/152.58; 73/632; 702/48; 702/81

(58) Field of Classification Search
CPC .............. G01N 2291/02827; G01N 2291/102; G01N 2291/2626; G01N 29/07; G01N 29/2223; G01N 33/36; G01N 3/08; G01N 2291/02854; G01N 2291/042; G01N 2291/0421; G01N 29/348; G01N 29/4454; G01N 2291/014; G01N 2291/015; G01N 29/14; G01N 29/223; G01N 29/38; B66C 13/16; B66C 15/00; B66C 15/06; B66D 1/54; G01B 17/04; G01K 11/24; G01K 2217/00; B63B 21/66; B63G 8/42; G01V 1/3826; G01V 1/50
USPC ........... 702/34, 35, 46, 48, 54, 66, 67, 71, 72, 702/73, 75, 79, 81, 96, 103, 104, 142, 149, 702/157, 159, 171, 39, 182; 73/152.58, 73/579, 59, 632, 769; 324/535
See application file for complete search history.

(56) References Cited

U.S. PATENT DOCUMENTS 5,257,544 A  11/1993  Khuri-Yakub
(Continued)

FOREIGN PATENT DOCUMENTS

WO  89/04960 A1  6/1989
WO  0186280     11/2001

OTHER PUBLICATIONS

International Written Opinion in connection with PCT/US2010/033767.
(Continued)

*Primary Examiner* — John H Le
(74) *Attorney, Agent, or Firm* — Michael Best & Friedrich LLP

(57) ABSTRACT

A non-contact signal propagation property evaluation system for ropes can be deployed for a number of different applications including, but not limited to, moving lines, e.g., crane or winch and static lines, e.g., mooring lines, stays, etc., to evaluate physical properties of the ropes and, in some cases, to help evaluate structural health of the ropes. The system includes a first transducer for generating ultrasonic waves, a second transducer for receiving ultrasonic waves propagated transversely through and around the rope, and a processor executing computer readable code to determine acoustic propagation properties of the rope.

19 Claims, 9 Drawing Sheets

(56) References Cited

U.S. PATENT DOCUMENTS

| | | | |
|---|---|---|---|
| 5,824,908 A | | 10/1998 | Schindel |
| 6,082,193 A | * | 7/2000 | Paulson .................... 73/152.58 |
| 6,276,209 B1 | | 8/2001 | Schafer et al. |
| 2001/0047691 A1 | | 12/2001 | Dzenis |
| 2003/0052695 A1 | | 3/2003 | Smith |

OTHER PUBLICATIONS

Database Compendex; Engineering Information, Inc., NY, NY; 1984; Williams Jr. James H. et al.: "Ultrasonic Wave Velocity in Double-Braided Nylon Rope."; XP002610452; Database accession No. EIX84090148228; & Fibre Science and Technology 1984;, vol. 21, No. 1, 1984.

Ferreira M et al.: "Nondestructive Testing of Polyaramide Cables by Longitudinal Waved Propagation: Study of the Dynamic Modulus"; Polymer Engineering and Science, Brookfield Center, US, vol. 40, No. 7, Jul. 1 2000; pp. 1628-1634; XP000969794; ISSN: 0032-3888; DOI: DOI:10.1002/PEN.11294.

First Office Action from the Australian Intellectual Property Office for Application No. 2010245947 dated Dec. 24, 2013 (4pages).

Second Office Action from the Australian Intellectual Property Office for Application No. 2010245947 dated May 23, 2014 (4 pages).

* cited by examiner

NON-CONTACT ACOUSTIC SIGNAL PROPAGATION PROPERTY EVALUATION OF SYNTHETIC FIBER ROPE

CROSS-REFERENCE TO RELATED APPLICATIONS

This application represents the national stage entry of PCT International Application No. PCT/US2010/033767 filed May 5, 2010 which claims the benefit of U.S. Provisional Application 61/215,496 filed May 6, 2009, and U.S. Provisional Patent Application No. 61/215,527 filed May 5, 2009, the disclosures of which are hereby incorporated by reference in their entirety all of which are hereby incorporated herein by reference for all purposes.

STATEMENT CONCERNING FEDERALLY SPONSORED RESEARCH OR DEVELOPMENT

Not applicable.

FIELD OF THE INVENTION

The present invention relates to a non-contact system for evaluating acoustic signal propagation properties through high performance synthetic fiber ropes or cables. Such a system can be used for non-destructive evaluation (NDE) and structural health monitoring (SHM) of synthetic fiber ropes and cables. Such a system can be used in conjunction with application-specific operating characteristics to establish retirement criteria for the synthetic ropes and cables used in those applications.

BACKGROUND OF THE INVENTION

The lightweight nature of synthetic fiber rope provides many performance and economic advantages over metal wire rope. For example, when used in conjunction with sheaves in applications known as cyclic bend over sheave (CBOS) applications (e.g., cranes, elevators, heave compensation systems, and pulling lines), synthetic fiber rope allows for the use of equipment having a smaller footprint, less weight, and less power consumption than similar equipment for metal wire rope. However, regardless of whether metal wire or synthetic fiber rope is used in a particular application, it is critical to be able to assess the rope's condition to provide and maintain a retirement criteria to assure safe operation of the rope.

A crucial and dynamic component used for determining and maintaining an accurate retirement criteria is the structural integrity of the rope. The integrity of the rope is used in conjunction with other components including user preferences (e.g., replacement at 50% strength, etc.) and the particular application, (e.g., mooring, cranes and winches, safety lines, etc.) to determine the retirement criteria.

A number of SHM and NDE systems and methods that measure rope and cable structural integrity to determine the retirement criteria of steel and other metallic wire ropes have been developed. However, there are no generally accepted methods of measuring structural integrity for synthetic ropes, and thus the general practice for determining retirement criteria for synthetic fiber ropes relies on visual inspections and/or by tracking the history of usage for each rope. Visual inspections are inherently subjective and history-of-usage tracking can be highly inaccurate, therefore current retirement criteria are not based on meaningful parameters.

Responsive to the deficiencies of visual inspections and history of usage tracking, a number of objective methods for SHM and NDE for synthetic fiber ropes have been developed. The methods use secondary materials such as conductive carbon fibers and glass or polymeric optical fibers intertwined with the synthetic fibers of the rope. In theory, the secondary materials undergo the same stresses and wear as the synthetic fibers. The stresses on the secondary materials can be easily measured and from these measurements the stresses and wear on the synthetic fibers is inferred. In reality, because the materials are inherently different and due to the complicated structure of the rope, the synthetic fibers can undergo stresses and wear that the secondary materials do not. Furthermore, the secondary materials are only exposed to stresses in their immediate vicinity and, as such, there may be sections of the rope in which stresses and wear are not measured. For these reasons, measurements obtained using secondary materials directly reflect the integrity of the evaluation materials only and indirectly reflect that of the synthetic fibers that make up the rope itself. Furthermore, synthetic fiber ropes intertwined with secondary materials may be less strong, have different than expected abrasion properties, and be more difficult to manufacture than ropes formed entirely from synthetic fibers. For at least these reasons, methods for measuring the structural integrity of rope with optical fibers are not widely practiced.

Another method of monitoring and evaluating synthetic fiber ropes involves longitudinal waves propagated over a length of rope. Such a method may utilize longitudinal wave propagation theory such as described by M. Ferreira et al. in "Non Destructive Testing of Polyaramide Cables by Longitudinal Wave Propagation: Study of the Dynamic Modulus", Polymer Engineering and Science, Vol 40, No. 7, July 2000. This method calls for at least some physical contact with the rope as probes or tappers directly contact the rope to introduce the acoustic signal. Furthermore, to determine meaningful retirement criteria with data from longitudinal waves, the rope must be held under constant tension (e.g., elevator cables, antenna stays, etc.) when being evaluated. This limits the use of this method to applications monitoring a stationary length of rope. Even then, vibrations in the rope introduced by devices in the rope's environment, such as motors and sheaves, are picked up by the transducers, resulting in distorted wave measurements. A further deficiency of this method is that it measures the entire length of the rope between the transducer and receiver, which are normally placed at each end of the rope. Therefore the resolution of this system is limited by the distance between the transducer and receiver. If only a small part of the rope is damaged, the system would not be able to indicate the specific location of the damage and the entire rope would have to be considered suspect. Another limitation to this method is that it cannot be used in situations where a portion of the rope is inaccessible, such as a rope used in conjunction with an offshore crane where one end could be under thousands of feet of water.

Therefore, there is a need for a system that enables structural health monitoring of synthetic fiber ropes in a way that does not need to have direct contact with the rope, access to two distinct points along the rope, or the use of secondary materials, with greater resolution, and furthermore, is able to be used on a fast moving rope, and with a variety of rope fibers and construction methods.

SUMMARY OF THE INVENTION

According to one aspect of the present invention, a non-contact acoustic signal propagation property evaluation system for synthetic ropes includes a first non-contact transducer spaced from a side of a rope to be evaluated. A first electrical signal is generated by a signal generator. The first transducer converts the first electrical signal from the signal generator into an acoustic signal directed towards the rope. A first portion of the acoustic signal propagates through the rope in a transverse direction and a second portion of the acoustic signal passes around the perimeter of the rope. A second transducer is spaced from an opposite side of the rope and is radially aligned with the first transducer. The second transducer receives and converts the first and second portions of the acoustic signal into a second electrical signal. A signal processing circuit receives and converts the second electrical signal into a digital signal. A processor connected to the signal processing circuit and executing computer readable code attributes properties of the digital signal to the acoustic propagation properties of the rope which can then be used to determine the physical properties of the rope.

The acoustic signal may be an ultrasonic waveform and the first portion of the acoustic signal may be a longitudinal ultrasonic wave. The first and second transducers may be fixed in place while the rope moves relative to the first and second transducers. Additional transducers may be used in the system, such as a third transducer spaced from the rope and the first transducer and a fourth transducer spaced from the rope and the second transducer. The first transducer and the second transducer may be positioned at a first longitudinal location of the rope, and the third transducer and the fourth transducer may be positioned at a second longitudinal location of the rope. In some embodiments, the first electrical signal is either a pulse, square, or a sinusoidal waveform. The code may further provide a structural health measure of the rope based in part on the acoustic propagation properties of the rope. The first transducer and the second transducer may be piezoelectric-based transducers. A first air gap may be disposed between the first transducer and the rope, and a second air gap may be disposed between the second transducer and the rope.

According to another aspect of the present invention, a method of evaluating acoustic signal propagation properties through a rope comprises the steps of: generating, at a first location spaced apart from the rope, an acoustic signal; directing the acoustic signal in a transverse direction towards a first longitudinal location of the rope, wherein upon impinging the rope, a first portion of the acoustic signal propagates through the rope and a second portion of the acoustic signal passes around the perimeter of the rope; receiving, at a second location spaced from the rope, the first portion and the second portion of the acoustic signal; and analyzing the first portion and the second portion of the acoustic signal.

The steps of generating, directing, receiving, and analyzing may be repeated at each of a plurality of longitudinal locations along the rope. The steps of generating, directing, receiving, and analyzing may be repeated at the first longitudinal location of the rope and the step of analyzing may include analyzing changes in the first portion and the second portion of the acoustic signal over time. The step of analyzing may include determining a rate of change of the first portion and the second portion of the acoustic signal. The step of analyzing may include comparing the first portion and the second portion of the acoustic signal to reference data. The step of generating the acoustic signal may include generating the acoustic signal using a first transducer spaced from the rope. The step of receiving the first portion and the second portion of the acoustic signal may include receiving the first portion and the second portion of the acoustic signal using a second transducer spaced from the rope opposite the first transducer. The method may further comprise the step of moving the first transducer and the second transducer while the rope remains stationary. The method may further comprise the step of determining a structural health measure of the rope based, at least in part, on the first portion and the second portion of the acoustic signal. The step of directing may include directing the acoustic signal through a water gap between the first location and the rope.

The foregoing and other objects and advantages of the invention will appear in the detailed description that follows. In the description, reference is made to the accompanying drawings that illustrate a preferred embodiment of the invention.

BRIEF DESCRIPTION OF THE DRAWINGS

FIG. 8b shows another perspective view of the fixture of FIG. 8a.

DETAILED DESCRIPTION OF THE PREFERRED EMBODIMENT

Unlike the aforementioned prior art systems that measure longitudinal or shear ultrasonic waves traveling along the length of a rope using probes or tappers in physical contact with the rope, the present invention relies on the generation and measurement of acoustic signals propagating transversely through the longitudinal axis of the rope and transversely around the perimeter of the rope using non-contact means.

Figure 1A:
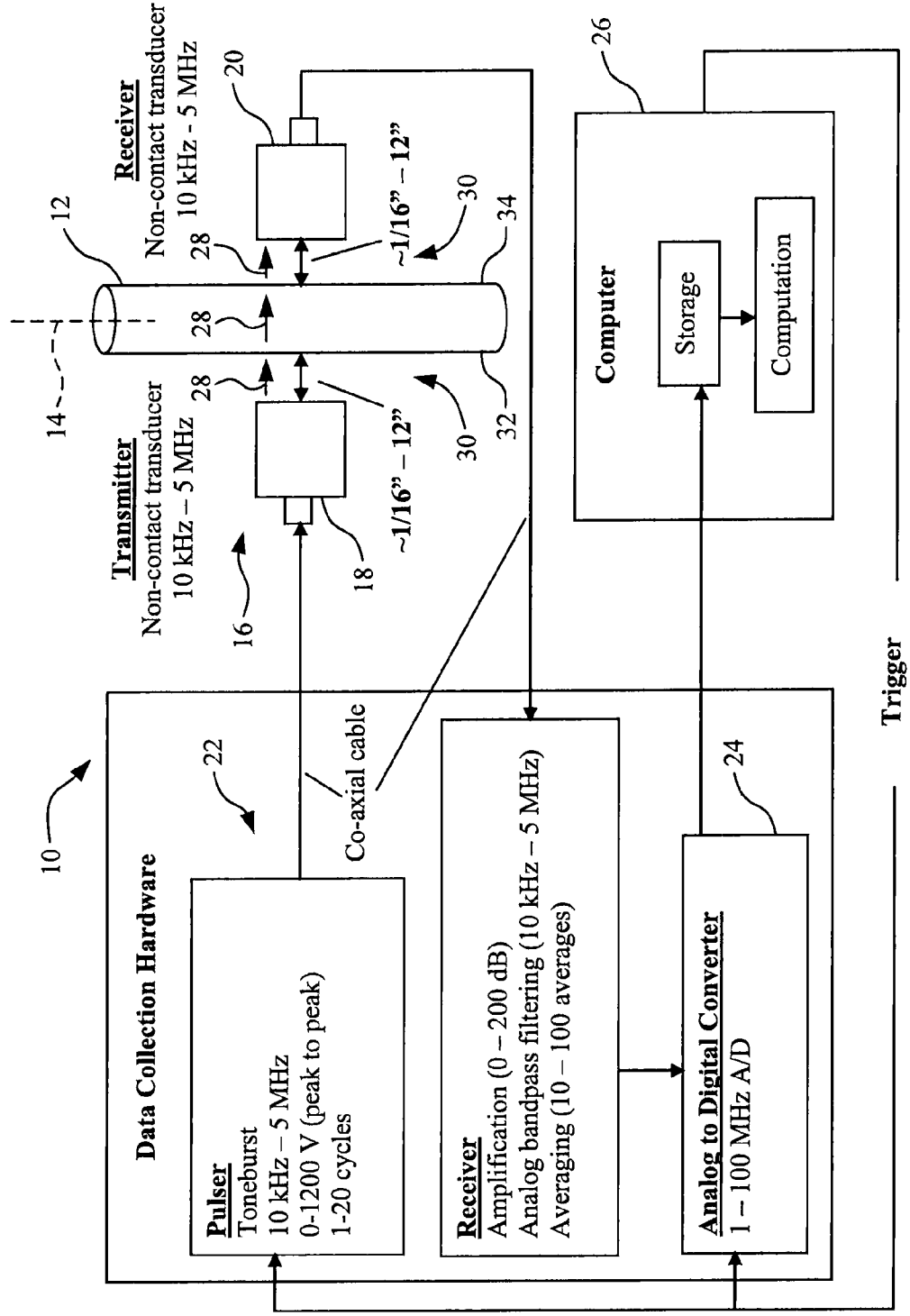
FIG. 1a shows a first exemplary embodiment of a configuration of various components of a non-contact acoustic signal propagation property evaluation system in accordance with the present invention.
Figure 1B:
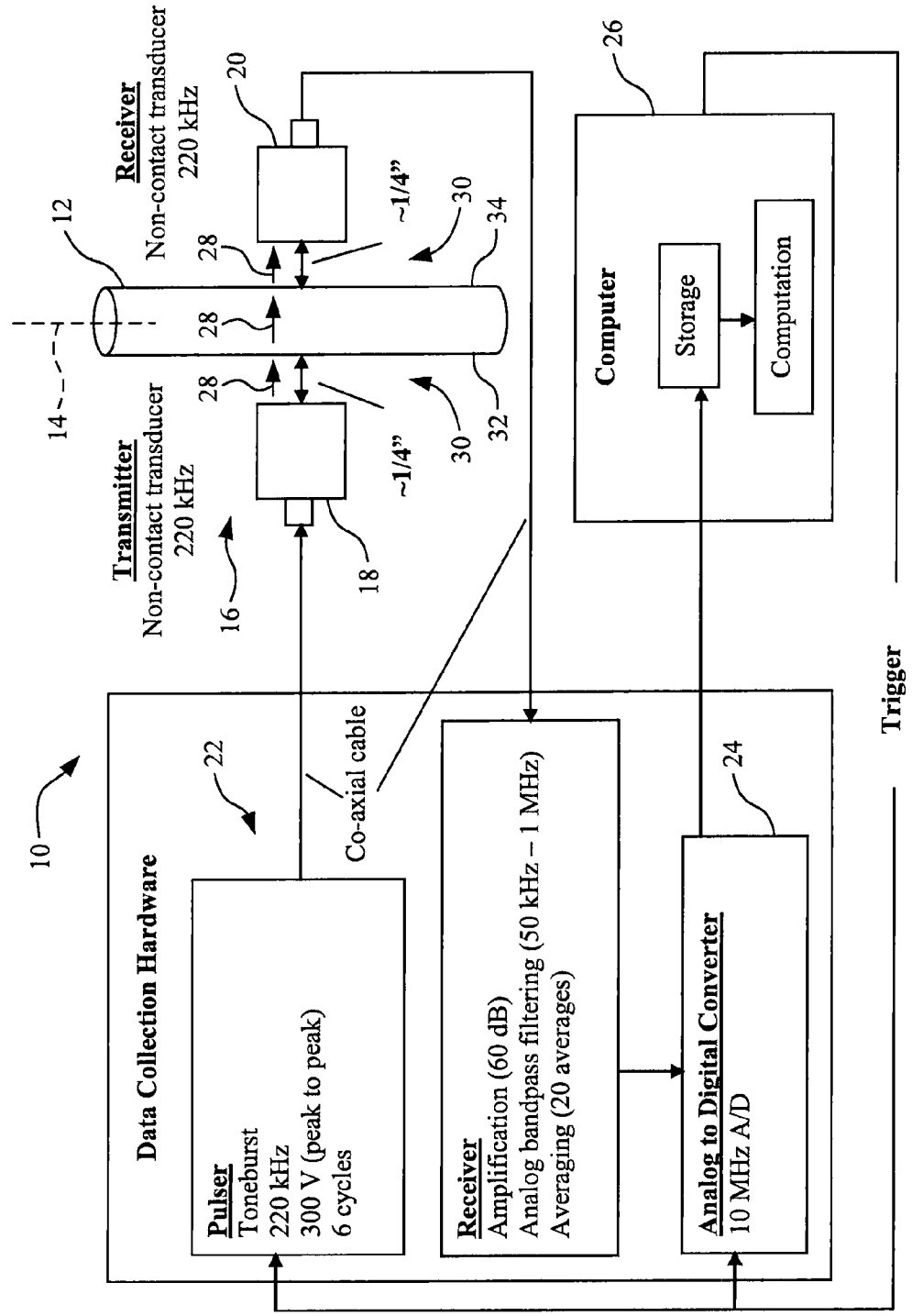
FIG. 1b shows a second exemplary embodiment of a configuration of the various components of the non-contact acoustic signal propagation property evaluation system.
Figure 1C:
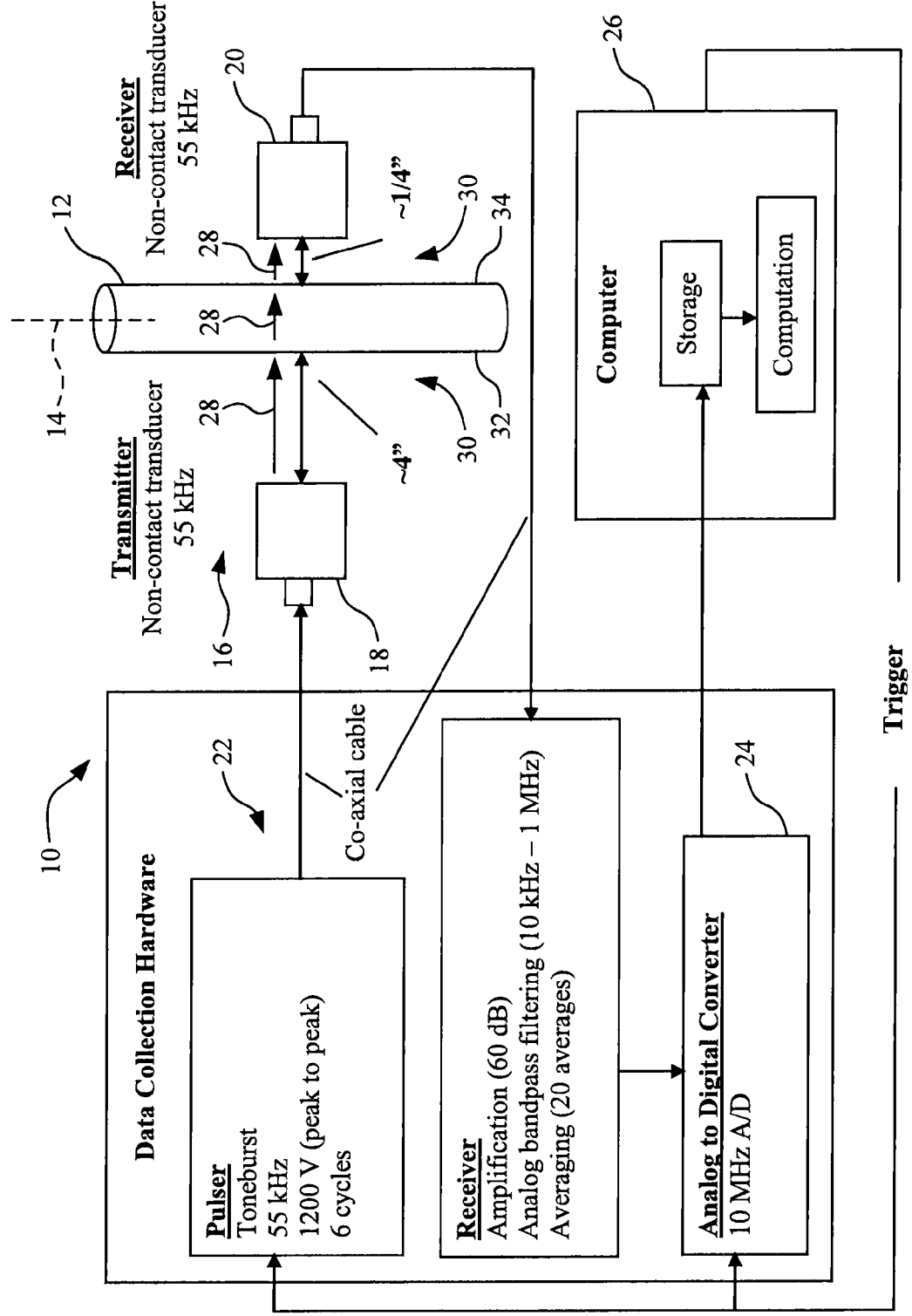
FIG. 1c shows a third exemplary embodiment of a configuration of the various components of the non-contact acoustic signal propagation property evaluation system.

Referring initially to FIGS. 1a-1c, a non-contact acoustic signal propagation property evaluation system 10 according to the present invention monitors and evaluates a synthetic fiber rope 12 (or cable; only the term "rope" is used herein for simplicity) moving along a longitudinal axis 14. The system 10 includes a first transducer pair 16 operating in a through-transmission mode with radially-aligned transducers 18, 20 positioned on opposite sides of the rope 12. The system 10 further includes a combined signal generator and receiver unit 22 (e.g., an ultrasonic signal generator and receiver unit) and a signal processing circuit 24 (e.g., an analog to digital converter). The system 10 further includes a software application operating on a processor 26 (e.g., a personal computer) to collect signal propagation property data. In some embodiments, the software application uses the data, in addition to other parameters, to evaluate the structural health of the rope 12.

Suitable non-contact transducers include commercially available ultrasonic transducers. A preferred non-contact transducer has an active area of one inch by one inch, a 100-300 kHz resonant frequency, a 200 kHz nominal frequency, and is positioned a quarter inch from the rope 12. An alternative preferred non-contact transducer has an active areas of four inches by two inches, a 50 kHz resonant frequency, and is positioned four inches from the rope. A suitable signal generator, receiver, and converter includes a commercially available ultrasonic testing PCI board mounted in a PC chassis with an ultrasonic toneburst pulser/receiver unit and high speed analog to digital converter. A preferred pulser/receiver unit has a 0-300 V peak to peak sinusoidal or square wave output, a 20 kHz to 6.5 MHz pulse frequency, and a 0-15 pulse cycles capability. If additional signal strength is needed to overcome environmental noise or highly attenuative synthetic media, an amplifier can be used to increase the pulsing voltage to 1200 V. A preferred analog to digital converter has up to a 100 MHz sampling resolution. A suitable software application for collecting and extracting rope data includes the UTerminal or Utomography software package commercially available from FBS, Inc. of State College, Pa. Other suitable software applications can be off the shelf data acquisition programs that can be configured to acquire and interpret ultrasonic data in accordance with known phenomena, such as found in "Ultrasonic Waves in Solid Media" 1999 by Joseph L. Rose, the contents of which are fully incorporated herein by reference.

In the embodiments described in the previous paragraph, the software application running on the PC 26 triggers the pulser/receiver unit 22 to generate an electrical pulse which is transmitted to the first air-coupled transducer 18. Alternatively, a windowed sinusoid of a particular frequency may be used. The first transducer 18 converts the electrical excitation pulse into an acoustic energy wave, i.e., ultrasonic pulse signal 28, directed towards the rope 12. The ultrasonic pulse signal 28 travels through an air gap 30 surrounding the rope 12, reaches a near surface 32 and propagates into the rope 12.

A large acoustical impedance mismatch between the air gap 30 and the rope 12 causes a portion of the ultrasonic signal 28 to be reflected back from the rope 12 and another portion to travel around the rope 12. Signal losses are minimized by reducing the size of the air gap 30, using focused transducers, matching the size of the transducer 18 with the width of the rope 12, adjusting the signal frequency or amplitude of the pulse signal 28, and using high resolution receiving hardware (e.g., hardware having a high sample rate, a high digitizing rate, etc.).

The portion of the ultrasonic signal 28 that propagates into the rope 12 is further divided into various elastic waveforms including shear waves, not illustrated, travelling through the rope 12 along the axis 14 and surface waves, not illustrated, that travel circumferentially along the surface of the rope 12. Some of the energy traveling around the rope does not interact with the rope 12 and only travels through the air. All of these ultrasonic signals, the waves traveling through the rope, on the surface of the rope, or in the air around the rope, can be received by the receiving transducer 20, recorded, and analyzed to aide in predicting the structural health of the rope 12. Of particular interest, however, is the pulse signal 28 that propagates through the rope 12 laterally, or transverse to the rope's longitudinal axis 14. Upon reaching a far surface 34 of the rope 12, the propagating pulse signal 28 continues through the air gap 24 and is received by the second, receiving air-coupled transducer 20.

The receiving transducer 20 is triggered to collect the ultrasonic signal 28 by the pulser/receiver unit 22 at a predetermined time interval or when the portion of the rope 12 of interest is at a particular position to allow for measurement. In a preferred embodiment, ninety-nine pulse signals 28, occurring over one and a half seconds, are received over a given length of the rope 12 and spatially averaged together. The averaged analog signal is filtered and amplified by the pulser/receiver unit 22 and converted into a digital signal by the analog to digital converter 24. The digital signal, representing the data point for one cycle, or, alternatively, one particular position, is collected and stored in memory of the PC 26.

Figure 2:
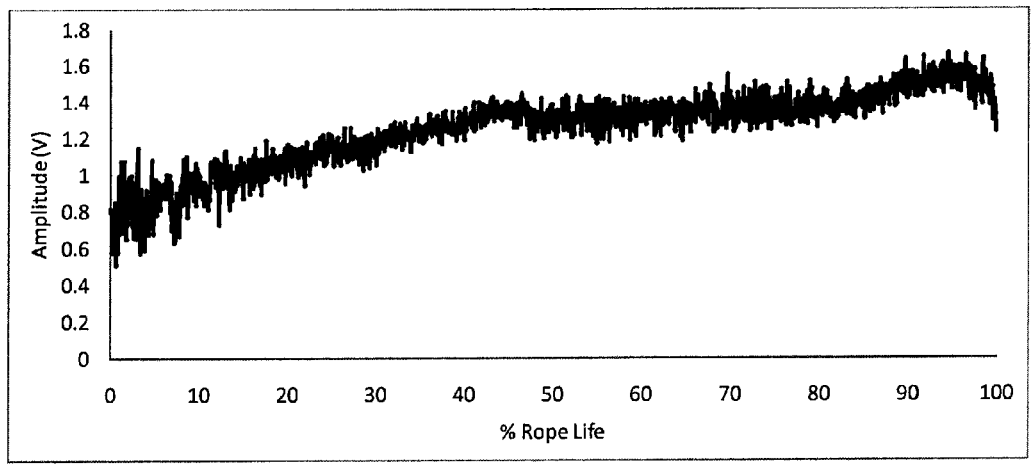
FIG. 2 illustrates the amplitude of the ultrasonic signals propagated through a 0.75" diameter synthetic fiber rope at one specific location as a function of rope life percentage obtained using the configuration shown in FIG. 1.
Figure 3:
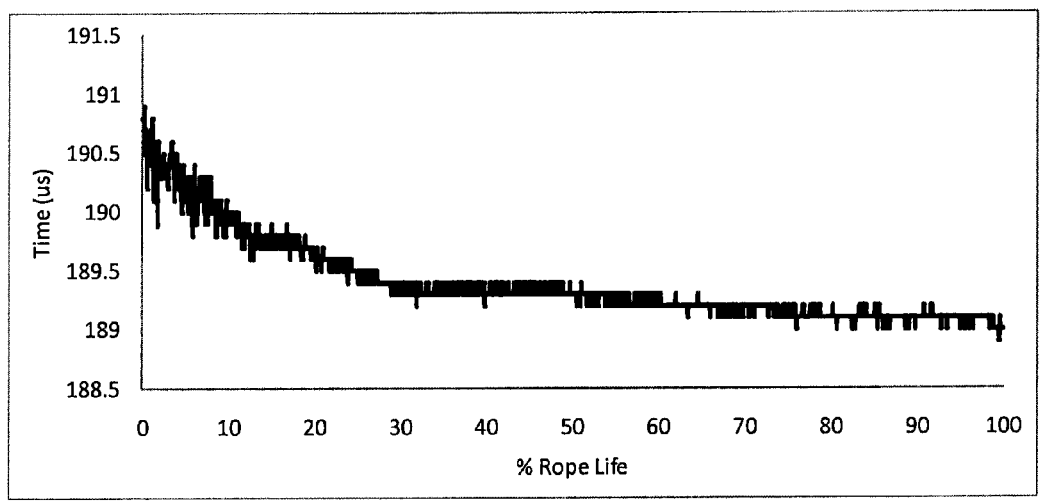
FIG. 3 illustrates the arrival time of the ultrasonic signals of FIG. 2 as a function of rope life percentage.

The software application extracts information, including amplitude and arrival time, from each data point and can be plotted against a measure of the cycle life of the rope 12. To extract the amplitude of each data point, a time-based window of the received radio frequency (RF) waveform is selected and the peak value of the signal is extracted. FIG. 2 is an exemplary graph of the signal amplitude of each data point at one specific location of the rope plotted as a function of rope life percentage. To extract the arrival time of each data point, a time window in the RF waveform is first selected for evaluation. The peak of the signal in this window is then determined and followed back to the preceding "zero crossing". The time corresponding to that zero crossing is extracted and plotted as a function of cycle number or position along the rope. FIG. 3 is an exemplary graph of the arrival time of each data point plotted as a function of rope life percentage. Other data point properties that may be further analyzed include the total received energy and signal frequency content.

The above data can be used in variety of manners. In some embodiments, the software application measures changes in the signal propagation property data of the rope 12 to evaluate the structural health of the rope 12. One key physical property of the rope 12 is the elastic modulus which is known to change over time in response to fiber fatigue. The amount of energy transmission and speed of the propagating pulse signal 28 is a factor of the density and modulus of the rope 12. Accordingly, the change in travel time of ultrasonic pulse signals over a range of frequencies can be used to determine the change in the modulus of the rope 12. Changes in the properties of the ultrasonic signals passing through and around the rope 12 over time can also be used to determine changes in the modulus, and thus the fatigue or wear of the rope 12. Alternatively, in the case where there is no previously collected data for a particular rope, the data can be compared to a known reference value to approximately determine the modulus, and thus the fatigue or wear of the rope 12.

Two other parameters known to affect ultrasonic signal propagation properties are "thinning", or diameter reduction, and the temperature of the rope. Rope diameter reduction could cause changes in the ultrasonic wave arrival time and amplitude at the receiving transducer 20. Likewise, the modulus of the rope 12 is affected by the internal rope temperature, which could change the ultrasonic signal propagation properties. Non-contact methods for measuring these variables include, but are not limited to, an infrared thermometer or an optical pyrometer for measuring temperatures and air-coupled transducers in pulse-echo mode to measure the diameter of the rope 12. These and other physical parameters may be monitored, with these or other measurement techniques, and used to establish correction factors, if needed, for the received ultrasonic pulse signals.

The software application may operate in a rope health mode whereby an initial reference data set acquired for the rope 12 prior to, or immediately after, being put in service is used as a reference data set. Subsequent data sets are then compared to the reference data set. The health of the rope 12 is determined based on changes in the signal properties over time. The software may also operate in a non-destructive testing mode whereby the data sets are compared to predetermined threshold values to determine the health of the rope 12. The threshold values are stored in a database and may be determined by scanning a set of rope samples under known conditions.

Furthermore, the software application may provide the ultrasonic signal propagation data as another parameter for the retirement criteria for a rope 12 in a particular application. That is, the ultrasonic signal propagation properties of a rope may be monitored, along with other parameters, such as, but not limited to, the tension the rope has been under, the number of cycles over a sheave, the time the rope has been in service, to determine when a rope should be taken out of service. In such a case, the software application may operate in one or both of the above modes, and the rope 12 is taken out of service and replaced based on a predetermined retirement criteria based on all the factors listed herein.

Pattern recognition routines may be employed by the software application to help analyze the received signals, evaluate ultrasonic signal propagation properties, and, in some cases, monitor the health of the rope. Signal properties and features can be statistical or probabilistic in nature such as the skewness, Kurtesis, or mean. Properties can also be drawn from time and/or frequency domains and from other sources such as a Hilbert transform, pulse duration, and/or rise or fall time. In addition, physical based properties derived from wave mechanics, e.g., wave velocity or arrival time as a function of frequency or at a particular frequency, frequency shifting compared to reference data, attenuation as a function of frequency, and the like, could be evaluated by the routines. In cases in which the software application evaluates the structural health of the rope, the benefit of using pattern recognition routines depends on the selection of meaningful signal properties for monitoring. Pattern recognition algorithms utilizing a linear discriminate approach, nearest neighbor rule, or measured neural net could be used.

The system 10 described above may be modified without departing from the scope of the invention. For example, instead of using piezoelectric-based transducers, other non-contact transducers may be used, such as electromagnetic and laser-based acoustic transducers. As another example, the system 10 could be water-sealed and use water-coupled transducers (e.g., hydrophones), particularly for underwater applications including subsea rope inspections and evaluations. Further still, acoustic transducers can be designed to work in other types of mediums, e.g., oil, and could also be considered depending on the application.

Figure 6:
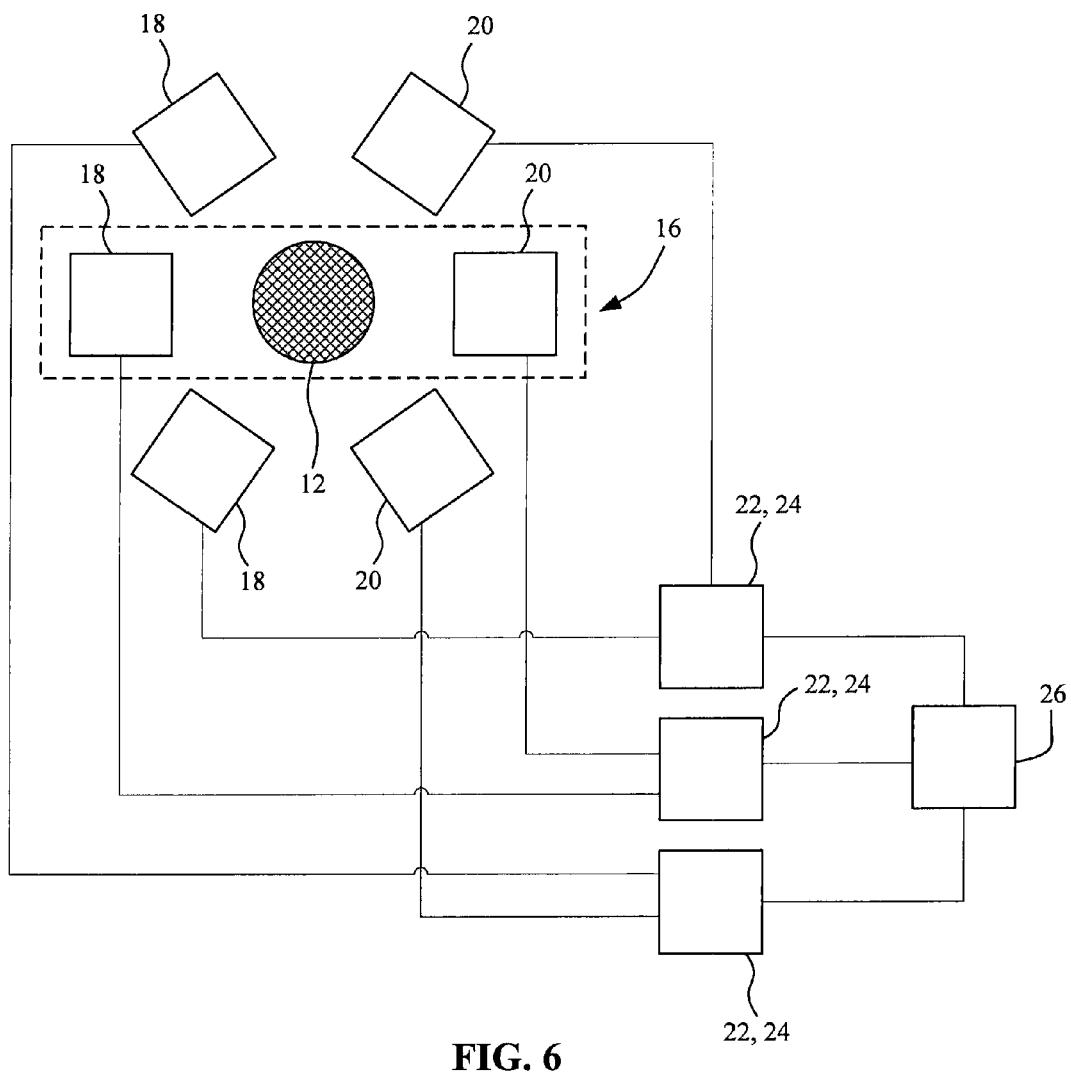
FIG. 6 shows another configuration of the non-contact acoustic signal propagation property evaluation system of FIG. 1 including multiple angularly disposed transducer pairs.
Figure 7:
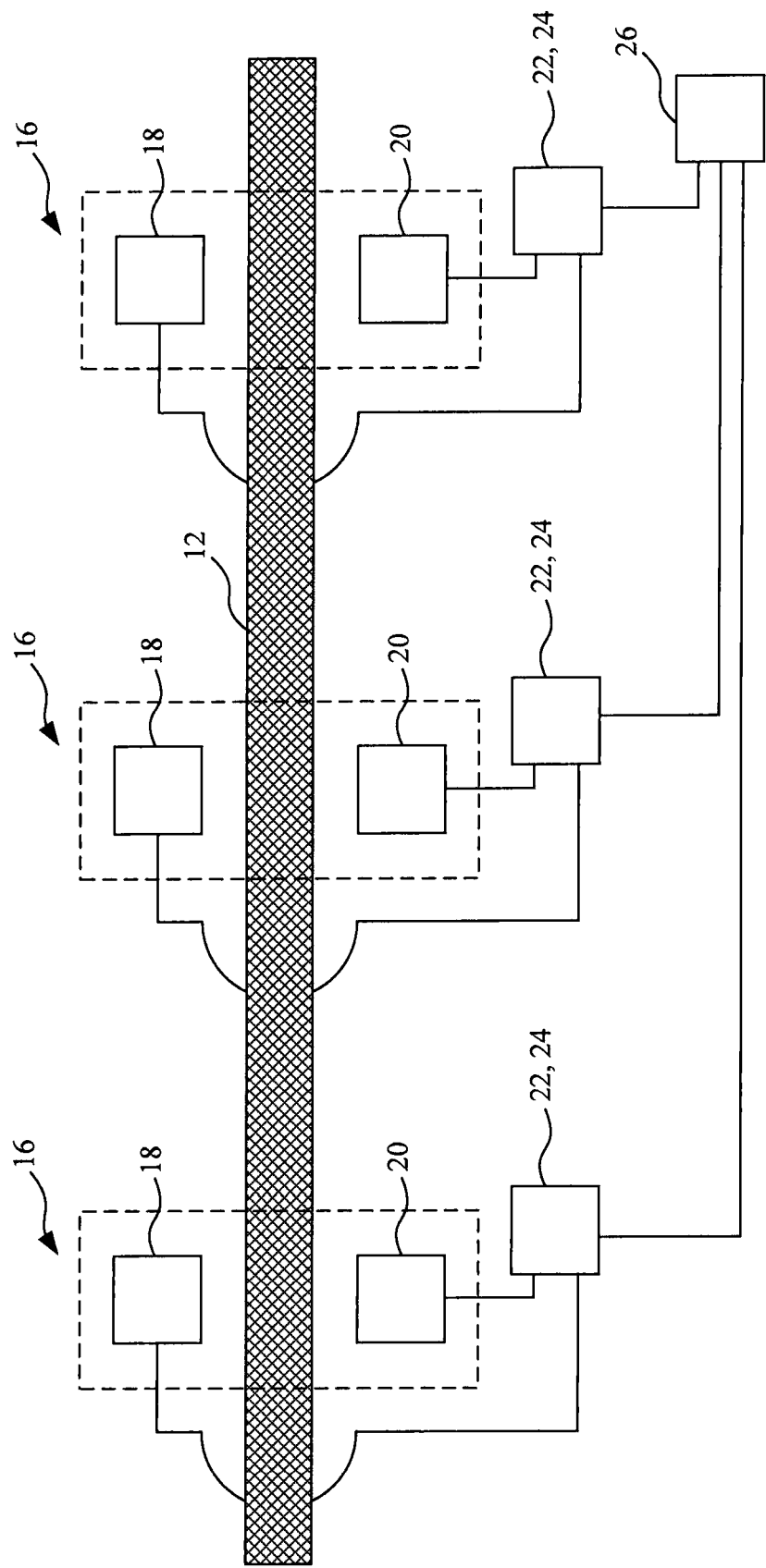
FIG. 7 shows another configuration of the non-contact acoustic signal propagation property evaluation system of FIG. 1 including multiple, axially spaced apart, transducer pairs.

An alternative transducer arrangement for the system 10 is shown in FIG. 6. As shown, additional transducer pairs 16 are provided and angularly spaced about the rope 12 to provide a "ring" arrangement. Such an arrangement may provide enhanced single point or spatial averaging via pulsed array operation. Another alternative transducer arrangement for the system 10 is shown in FIG. 7. As shown, additional transducer pairs 16 are provided and longitudinally spaced along the rope 12. With such an arrangement, multiple data values may be obtained for a single point of the moving rope 12 and averaged together. In each of these alternative arrangements, each transducer pair 16 could operate at a different frequency. Furthermore, these alternative arrangements could be combined to provide transducer rings at multiple longitudinal locations along the rope 12.

Figure 8A:
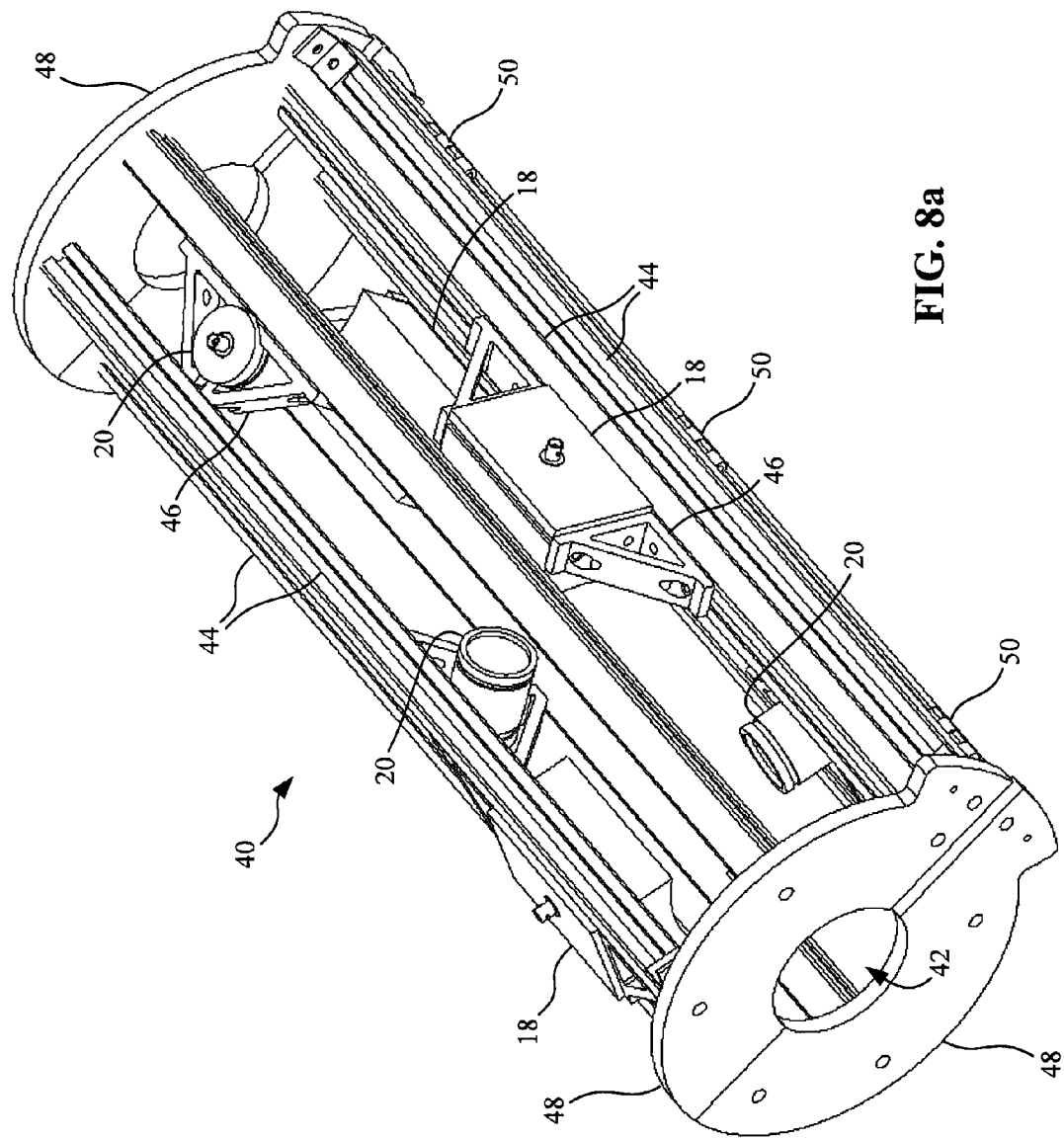
FIG. 8a shows a perspective view of a fixture supporting three axially spaced transducer pairs for monitoring a rope passing through the center of the fixture.
Figure 8B:
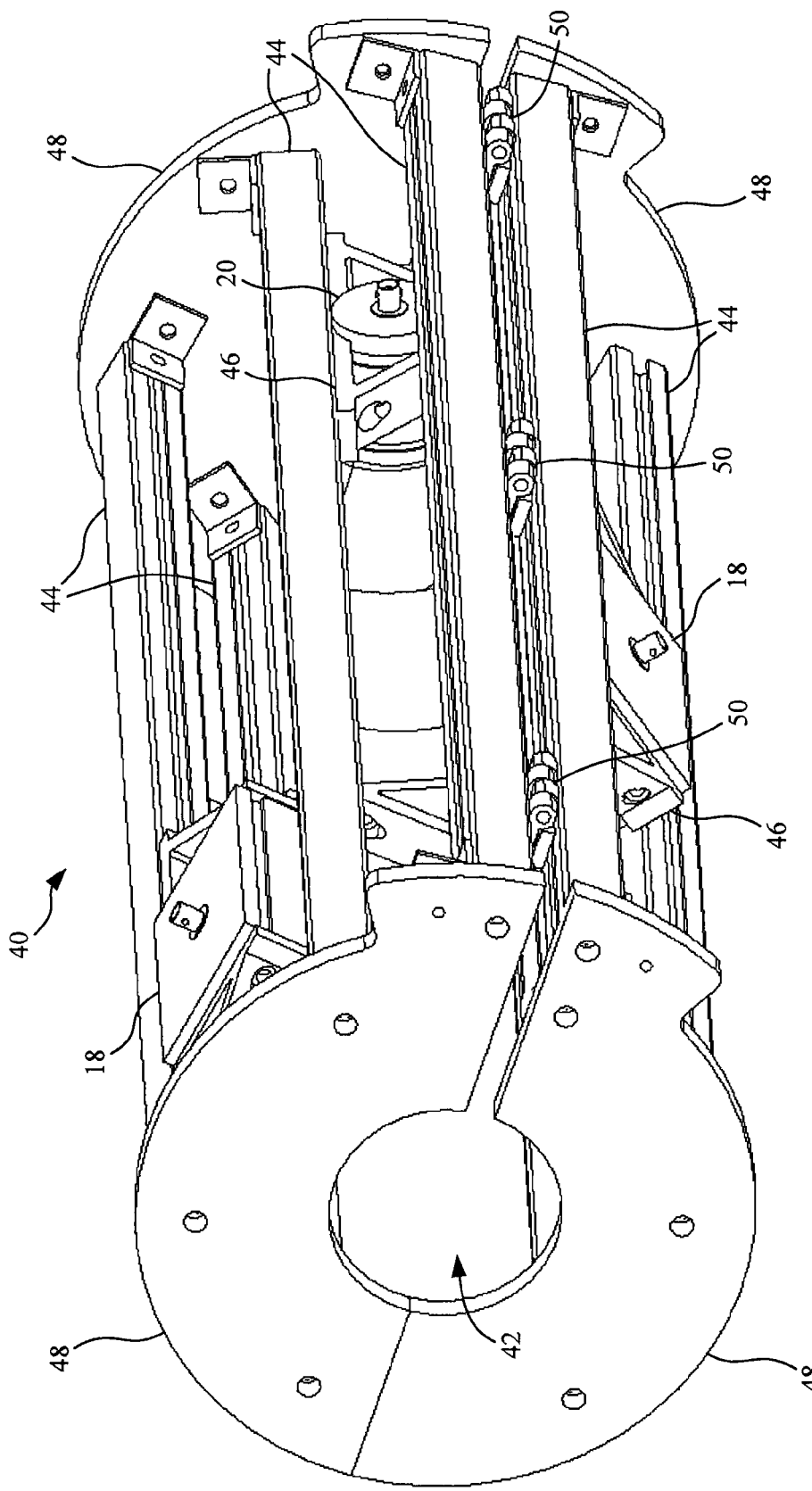

Referring to FIGS. 8a and 8b, the above transducer arrangements may be used in connection with a support fixture 40 having a passageway 42 through which the rope extends. The support fixture 40 includes a plurality of elongated supports 44 (e.g., extruded aluminum bars) that connect to angle bracket mounts 46 to support the transducers 18, 20. The transducers 18, 20 may be supported by different elongated supports 44. Furthermore, each transducer pair may be angularly offset (e.g., by 120 degrees) and longitudinally spaced from the other transducer pairs (i.e., positioned in different planes). The support fixture 40 also includes end plates 48 (e.g., aluminum plates) that mount the elongated supports 44. Two of the elongated supports 44 are preferably connected by hinges 50 that permit the fixture 40 to open, be placed around the rope, and connected to rope handling hardware (not shown).

In each of the above embodiments the transducer pair 16 may be fixed in place while the rope 12 moves relative to the transducers 18, 20. This suitable for applications such as, but not limited to, cranes and winches, where the rope 12 moves during use. Alternatively and in each of the above embodiments, the transducers 18, 20 are fixed relative to each other and move relative to a stationary rope 12. This suitable for applications such as, but not limited to, mooring, where the entire rope 12 is stationary.

Although the illustrated system 10 utilizes a through-transmission arrangement, other non-contact setups, such as a pulse/echo or shear wave arrangement, may be utilized. For example, a pulse/echo arrangement would allow for a reflection-coefficient evaluation method. In this case, a correlation between the amount of reflected ultrasonic waves and the integrity of the rope 12 could be developed and utilized. Such a method may be preferred in applications with significant rope thinning or if fewer transducers are desired.

Experimental Results

Figure 4:
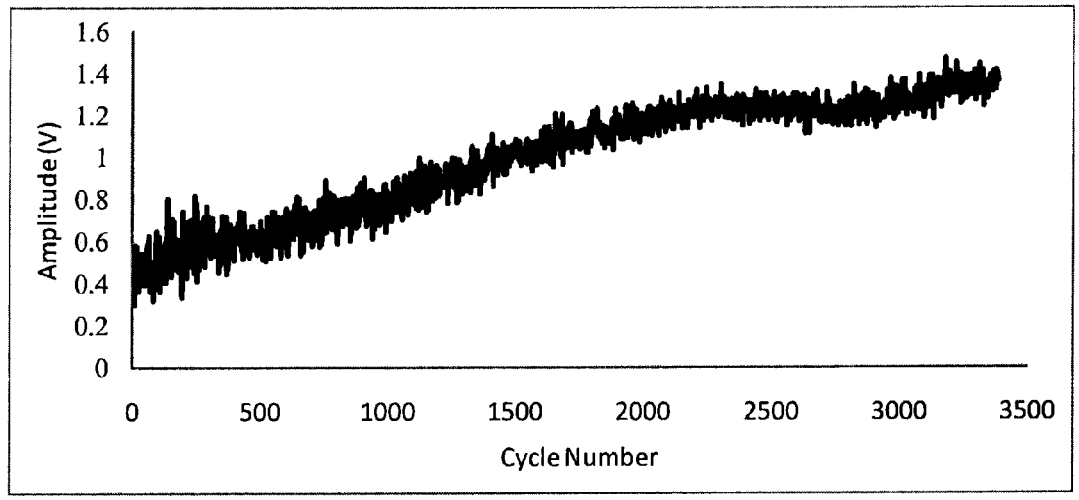
FIG. 4 illustrates the amplitude of the ultrasonic signals propagated through a 0.75" diameter synthetic fiber rope at one specific location as a function of rope cycle number.
Figure 5:
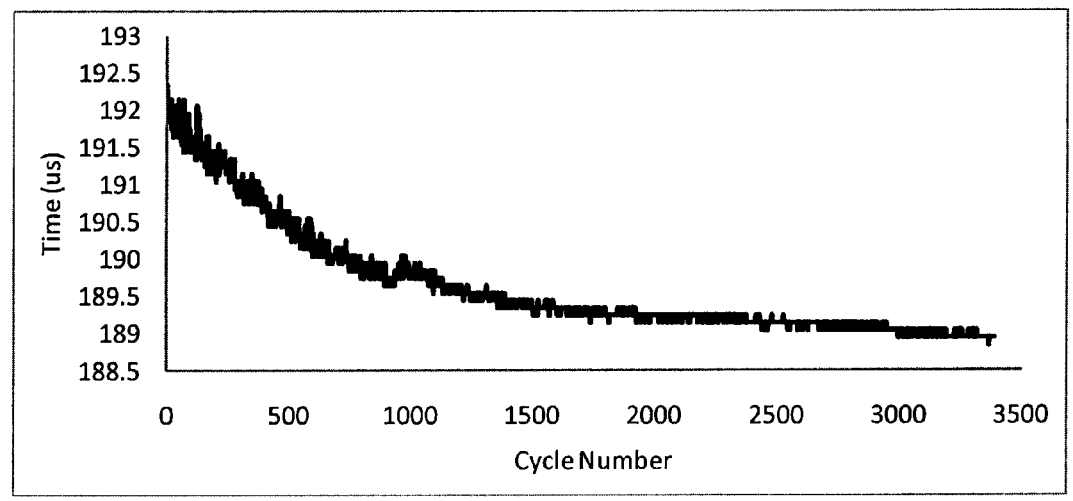
FIG. 5 illustrates the arrival time of the ultrasonic signals of FIG. 4 as a function of rope cycle number.

Several 0.75" diameter high-modulus polyethylene (HMPE) fiber ropes were cycled at six cycles per minute at a load of 7,000 pounds using a setup substantially as illustrated in FIG. 1. The rope typically failed and broke after 3,800 cycles. All the data was collected at the same location in each of the ropes used for the experiments. FIGS. 2 and 4 shows the amplitude of the data points of two separate samples. The data shows a consistent and predictable pattern. FIGS. 3 and 5 shows the arrival time from the data points for the same ropes as used for FIGS. 2 and 4, respectively. As with amplitude, arrival time changed in a consistent and predictable pattern. Given that the plots are generated using thousands of data points, the patterns are statistically significant.

From the above description, it should be apparent that the system according to the present invention uses non-contact ultrasonic transducers to measure the acoustic propagation properties through a synthetic rope. Furthermore, the acoustic propagation properties change in a measurable way as the rope or cable wears. This data can be used in conjunction with other factors to adjust retirement criteria for synthetic fiber rope. The system can be deployed in an onboard environment, such as on a marine vessel or oil rig, to measure changes to the physical properties, such as modulus, of the ropes used thereon. In some embodiments, the system includes a waveform generator, a first transducer for generating ultrasonic signals, a second transducer for receiving longitudinal ultrasonic signals propagated transversely through the rope and around the perimeter of the rope, and a processor utilizing algorithms to evaluate the acoustic propagation properties of the rope. In some embodiments, the non-contact and real-time measurements obtained by the system enables high-speed and reliable rope integrity determinations not possible with conventional visual inspection and history-of-use methods.

In some embodiments, the present invention provides a system that transmits, measures, and analyzes ultrasonic signals propagated transversely through the rope and around the perimeter of the rope. Specific features of the ultrasonic signal may be monitored over time to detect flaws or measure changes in the physical properties of the rope to, among other things but not limited to, predict remaining service life. Alternatively, specific features of the ultrasonic signal may be extracted and compared to a known reference value to detect flaws or estimate the current state of physical properties of the rope to, among other but not limited to, predict remaining service life. Signal features that could be used include, but are not limited to, signal amplitude, total received energy, signal arrival time or rope wave velocity, and signal frequency content. The use of one feature, or combinations of several features, may also be used to evaluate the physical properties of synthetic rope.

Preferred embodiments of the invention has been described in considerable detail. Although some attention was given to various alternatives within the scope of the invention, it is anticipated that one skilled in the art will likely realize alternatives that are now apparent from disclosure of embodiments of the invention. Accordingly, the scope of the invention is not limited by the above disclosure.

We claim:

1. A non-contact acoustic signal propagation property evaluation system for synthetic ropes, the system comprising:
   a first transducer spaced from a side of a rope to be evaluated, configured to convert a first electrical signal into an acoustic signal directed towards the rope, wherein a first portion of the acoustic signal propagates through the rope in a transverse direction and a second portion of the acoustic signal passes around the perimeter of the rope;
   a second transducer spaced from an opposite side of the rope and radially aligned with the first transducer, configured to receive and convert the first and second portions of the acoustic signal into a second electrical signal;
   a signal processing circuit configured to generate the first electrical signal and to receive and convert the second electrical signal into a digital signal;
   a processor connected to the signal processing circuit and executing computer readable code configured to attribute properties of the digital signal to acoustic propagation properties of the rope and provide a structural health measure of the rope based in part on the acoustic propagation properties of the rope.

2. The system of claim 1, wherein the acoustic signal is an ultrasonic waveform and wherein the first portion of the acoustic signal is a longitudinal ultrasonic wave.

3. The system of claim 1, wherein the first and second transducers are fixed in place and the rope moves relative to the first and second transducers.

4. The system of claim 1, further comprising:
   a third transducer spaced from the rope and the first transducer; and
   a fourth transducer spaced from the rope and the second transducer.

5. The system of claim 4, wherein the first transducer and the second transducer are positioned at a first longitudinal location of the rope, and the third transducer and the fourth transducer are positioned at a second longitudinal location of the rope.

6. The system of claim 1, wherein the first electrical signal is one of a pulse and a sinusoidal waveform.

7. The system of claim 1, wherein the first transducer and the second transducer are piezoelectric-based transducers.

8. The system of claim 1, further comprising:
   a first air gap disposed between the first transducer and the rope; and
   a second air gap disposed between the second transducer and the rope.

9. A method of evaluating acoustic signal propagation properties through a rope as the rope is used over time to monitor the structural health of the rope, the method comprising the steps of:
   generating, with a signal processing circuit, a first electrical signal;
   converting, with a first transducer and at a first location spaced apart from the rope, the first electrical signal into an acoustic signal;
   directing the acoustic signal in a transverse direction towards a first longitudinal location of the rope, wherein upon impinging the rope, a first portion of the acoustic signal propagates through the rope and a second portion of the acoustic signal passes around the perimeter of the rope;
   receiving, with a second transducer and at a second location spaced from the rope, the first portion and the second portion of the acoustic signal;
   converting, with the second transducer, the first portion and the second portion of the acoustic signal into a second electrical signal;
   receiving and converting, with the signal processing circuit, the second electrical signal into a digital signal;
   analyzing, with a processor, the digital signal representing the first portion and the second portion of the acoustic signal; and
   repeating the generating, converting, directing, receiving, converting, receiving, and analyzing steps over time as the rope wears to monitor changes in the first portion and the second portion of the acoustic signal and thereby determine structural health changes of the rope.

10. The method of claim 9, further including repeating the generating, directing, receiving, and analyzing steps at each of a plurality of longitudinal locations along the rope.

11. The method of claim 9, further comprising the step of determining a rate of change of the first portion and the second portion of the acoustic signal.

12. The method of claim 9, wherein the step of generating the acoustic signal includes generating the acoustic signal using a first transducer spaced from the rope.

13. The method of claim 12, wherein the step of receiving the first portion and the second portion of the acoustic signal includes receiving the first portion and the second portion of the acoustic signal using a second transducer spaced from the rope opposite the first transducer.

14. The method of claim 13, further comprising the step of moving the first transducer and the second transducer while the rope remains stationary.

15. The method of claim 9, wherein the step of directing includes directing the acoustic signal through a water gap between the first location and the rope.

16. The method of claim 9, wherein the acoustic signal propagation properties of the rope include an acoustic propagation speed, and the first portion and the second portion of the acoustic signal are based at least in part on the acoustic propagation speed.

17. The method of claim 9, wherein the step of repeating the generating, directing, receiving, and analyzing steps over time as the rope wears to monitor changes in the first portion and the second portion of the acoustic signal includes determining changes in the elastic modulus of the rope to thereby determine structural health changes of the rope.

18. The method of claim 9, wherein the step of repeating the generating, directing, receiving, and analyzing steps over time as the rope wears to monitor changes in the first portion and the second portion of the acoustic signal includes determining changes in the diameter of the rope to thereby determine structural health changes of the rope.

19. A non-contact acoustic signal propagation property evaluation system for synthetic ropes, the system comprising:

a first transducer spaced from a side of a rope to be evaluated, and configured to convert a first electrical signal into an acoustic signal directed towards the rope, wherein a first portion of the acoustic signal propagates through the rope in a transverse direction and a second portion of the acoustic signal passes around the perimeter of the rope;

a second transducer spaced from an opposite side of the rope and radially aligned with the first transducer, the second transducer configured to receive and convert the first and second portions of the acoustic signal into a second electrical signal a signal processing circuit configured to generate the first electrical signal and to receive and convert the second electrical signal into a digital signal; and a processor connected to the signal processing circuit and that is configured to determine acoustic propagation properties of the rope based on the second electrical signal and provide a structural health measure of the rope based on the acoustic propagation properties of the rope.

* * * * *